United States Patent [19]

Bradford et al.

[11] Patent Number: Plant 7,504

[45] Date of Patent: Apr. 23, 1991

[54] PLUM TREE (BLACK NOBLE)

[76] Inventors: Norman G. Bradford, 11875 E. Savana Rd.; Lowell G. Bradford, 12439 E. Savana Rd., both of Le Grand, Calif. 95333

[21] Appl. No.: 458,408

[22] Filed: Dec. 28, 1989

[51] Int. Cl.[5] ..... A01H 5/00

[52] U.S. Cl. ..... Plt./38

[58] Field of Search ..... Plt./38

[56] References Cited

U.S. PATENT DOCUMENTS

P.P. 2,539 6/1965 Anderson ..... Plt. 38

*Primary Examiner*—James R. Feyrer

[57] ABSTRACT

The present invention relates to a plum tree and more particularly to a new and distinct variety broadly characterized by a medium size, medium vigorous, hardy, productive, and regular bearing tree, which requires a pollinator. The fruit matures under the ecological conditions described in early June, with first picking on June 5, 1989, and is uniformly medium in size, clingstone in type, dark reddish purple in skin color, very smooth and shiny in surface appearance, attractive in shape, very sweet in flavor, and exceptionally firm in texture, resulting in excellent quality for keeping and shipping. The variety was developed as a hybridized seedling from the selected seed parent, Red Beaut (U.S. Plant Pat. No. 2,539), and an unnamed seedling as the selected pollen parent.

1 Drawing Sheet

BACKGROUND OF THE NEW VARIETY

In a continuing effort to improve the quality of shipping fruits, we, the inventors, typically hydridize a large number of nectarine, peach, plum, apricot, and cherry seedlings each year. The present invention relates to a new and distinct variety of plum tree, which has been denominated varietally as "Black Noble". The present variety was hybridized by us in 1983, and the resulting seedling was planted in a cultivated area of our experimental orchard at Bradford Farms near Le Grand, Calif., in Merced County (San Joaquin Valley). Specifically, the hybridized seedling was originated by using Red Beaut (U.S. Plant Pat. No. 2,539) as the selected seed parent and an unnamed seedling as the selected pollen parent. Subsequent to origination of the present variety of plum tree, we asexually reproduced it by budding and grafting, and such reproduction of plant and fruit characteristics were true to the original plant in all respects.

The present variety is similar to its selected seed parent, Red Beaut (U.S. Plant Pat. No. 2,539), by being self-sterile and by producing medium size fruit that is obovoid in shape, very shiny in surface appearance, and very firm in texture, but is distinguished therefrom by producing fruit that ripens seven days later, that is very dark reddish purple in skin color instead of red, that is red in flesh color instead of yellow, and that is much sweeter in flavor.

DRAWING

The accompanying photograph exhibits three whole fruits positioned to display the characteristics of the skin color and form; one fruit halved around the suture to reveal the flesh, stone, and stone cavity; and several leaves, all typical of the subject variety.

POMOLOGICAL CHARACTERISTICS

Referring now more specifically to the pomological characteristics of this new and distinct variety of plum tree, the following has been observed under the ecological conditions prevailing at the experimental orchard of the inventors near Le Grand, Merced County (San Joaquin Valley), Calif. All major color code designations are by reference to the Inter-Society Color Council, National Bureau of Standards. Common color names are also used occasionally.

TREE

Size: Medium.
Vigor: Vigorous.
Growth: Upright and dense.
Form: Vase formed.
Hardiness: Hardy.
Production: Productive, but requires a pollinator.
Bearing: Regular bearer.
Trunk:
- *Size.*—Medium.
- *Texture.*—Shaggy.
- *Color.*—Brownish gray [64. brGy].
- *Lenticels.*—Numerous. Color: Moderate reddish brown [43. m.rBr]. Average Size: 3/16" [4.8 mm.].

Branches:
- *Size.*—Medium.
- *Texture.*—Medium.
- *Color.*—1st year wood — Topside: Moderate brown [58. m.Br]. 1st year wood — Underside: Strong yellow green [117. s.YG]. Older wood: Strong brown [55. s.Br].
- *Lenticels.*—Numerous, very small.

Leaves:
- *Size.*—Medium. Average length: 4½" [114.3 mm.]. Average width: 1⅞" [47.6 mm.].
- *Thickness.*—Medium.
- *Form.*—Elliptical.
- *Apex.*—Acuminate.
- *Base.*—Acute.
- *Surface.*—Smooth.
- *Color.*—Dorsal surface: Moderate olive green [125m.01G]. Ventral surface: Moderate yellow green [120 m.YG].
- *Margin.*—Finely crenate.
- *Venation.*—Pinnately net veined.

*Petiole.*—Average length: 9/16" [14.3 mm.]. Average thickness: 1/16" [1.6 mm.].

*Glands.*—Average number: 2 to 4. Position: Some oppositely and some alternately positioned on petiole and base of blade. Size: Small. Form: Globose.

*Stipules.*—Numerous. Average length: 3/16" [4.8 mm.].

Flower buds:

*Hardiness.*—Hardy.

*Size.*—Medium.

*Length.*—Medium.

*Form.*—Free.

*Surface.*—Pubescent.

Flowers:

*Blooming period.*—Medium, as compared with other varieties.

*Date of first bloom.*—Mar. 1, 1989.

*Date of full bloom.*—Mar. 11, 1989.

*Size.*—Small.

*Color.*—White [263. White].

FRUIT

Maturity when described: Hard but eating ripe, June 8, 1989.

Date of first picking: June 5, 1989.

Date of last picking: June 11, 1989.

Size: Uniform, medium.

*Average diameter axially.*—1⅞" [47.6 mm.].

*Average traversely in suture plane.*—2⅛" [54.0 mm.].

Form: Uniform, symmetrical, obovoid.

*Longitudinal section form.*—Obovate.

*Transverse section through diameter.*—Round.

Suture: An inconspicuous line extending from the base but discontinues at the apex.

Ventral surface: Rounded, slightly lipped throughout.

Lips: Equal.

Cavity: Flaring, elongated in the suture plane with suture showing on one side.

Base: Cuneate and truncate.

Apex: Slightly prolonged, but rounded.

Pistil point: An inconspicuous dot marking the end of the suture line.

Stem: Medium size.

*Average length.*—⅜" [9.5 mm.].

*Average width.*—3/32" [2.4 mm.].

Skin:

*Thickness.*—Medium.

*Texture.*—Tough.

*Tenacity.*—Tenacious to flesh.

*Astringency.*—Strong.

*Tendency to crack.*—None observed as of yet.

*Bloom.*—Abundant (not shown in the drawing).

*Color.*—Very dark reddish purple [243. v.d.rP] with some dark orange yellow [72. d.OY] freckling more prominent near the apex.

Flesh:

*Color.*—Strong red [12. s.R] near the skin streaking into a moderate pink [5. m.Pk] near the pit, which darken with maturity.

*Surface color of pit cavity:* Grayish red [19. gy.R].

*Amygdalin.*—Scarce.

*Juice.*—Abundant, rich.

*Texture.*—Extremely firm, fine, very crisp.

*Fibers.*—Abundant, fine, tender.

*Ripens.*—Slightly earliest at apex.

*Flavor.*—Acidic and very sweet.

*Aroma.*—Moderate.

*Eating quality.*—Very best.

STONE

Type: Clingstone.

Form: Oval.

Base: Slightly oblique.

Apex: Sharply acute.

Sides: Equal, flattened.

Surface: Rugose, with a characteristic single groove along the ventral edge, and a single shallow groove along each side of the dorsal fin.

Color: Light yellowish brown [76. 1.yBr].

Pit wall: 1/16" [1.6 mm.] thick.

Tendency to split: Very slight.

Kernel:

*Form.*—Oval.

*Taste.*—Very bitter.

*Viable.*—Yes.

*Average width.*—5/16" [7.9 mm.].

Average length.—½" [12.7 mm.].

Skin color: Pale yellow [89. p.Y] before drying.

Pellicle color: Moderate yellowish brown [77. m.yBr].

Amygdalin: Abundant.

USE

Market: Fresh market, both local and long distance shipping.

Keeping quality: Excellent.

Shipping quality: Excellent.

Resistance to insects: No unusual susceptibilities noted.

Resistance to diseases: No unusual susceptibilities noted.

Although the new variety of plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of plum tree, substantially as illustrated and described, which is most similar to its selected seed parent, Red Beaut (U.S. Plant Pat. No. 2,539), by being self-sterile and by producing medium size fruit that is very attractive in shape, very shiny in surface appearance, and very firm in texture, but is distinguished therefrom and an improvement thereon by producing fruit that ripens seven days later, that is very dark reddish purple in skin color instead of red, that is red in flesh color instead of yellow, and that is much sweeter in flavor.

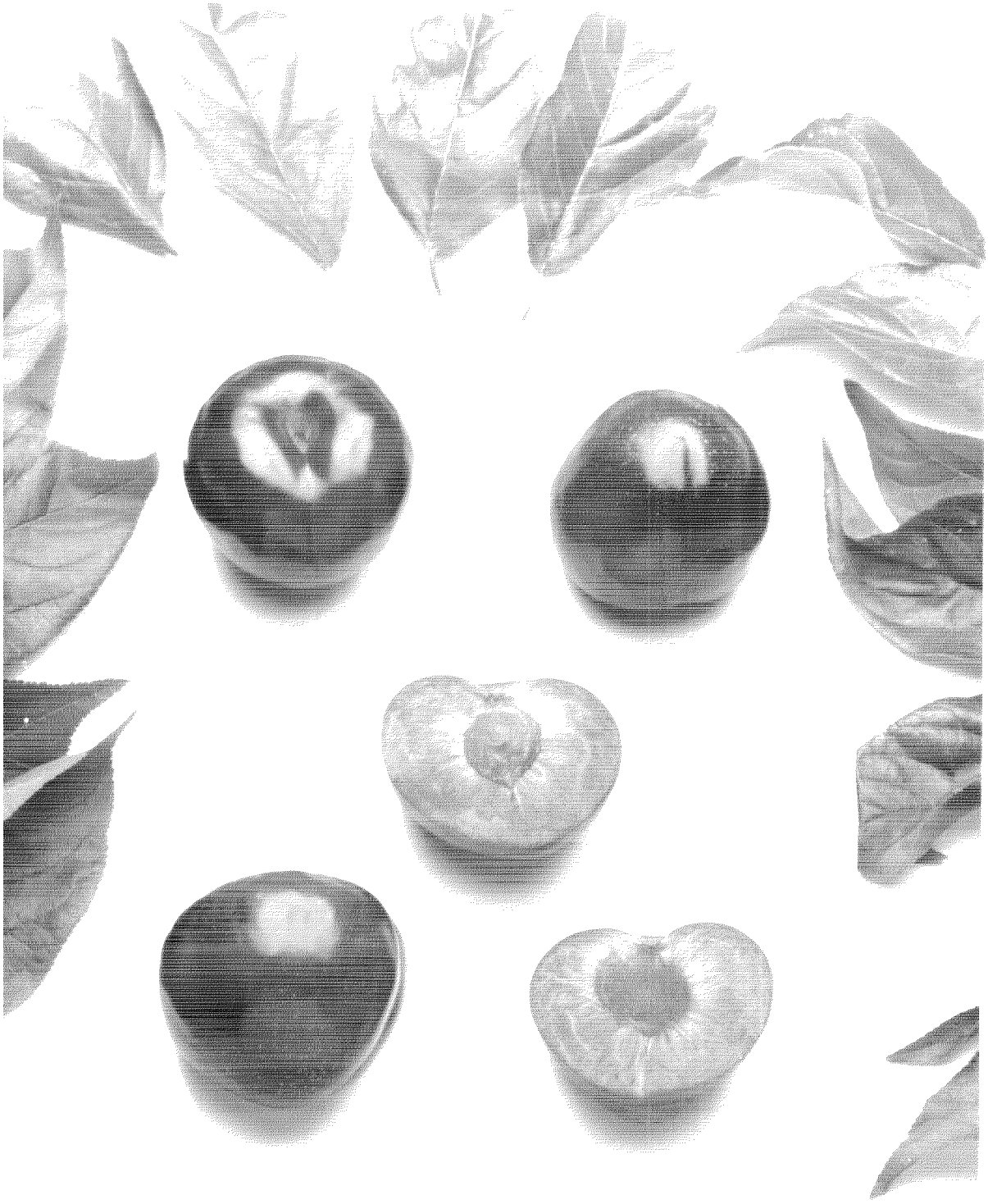

* * * * *